（12）United States Patent
Jeon et al.

(10) Patent No.: US 9,220,442 B2
(45) Date of Patent: Dec. 29, 2015

(54) THERMOTHERAPY DEVICE HAVING BODY SCAN FUNCTION AND METHOD FOR SCANNING BODY USING SAME

(75) Inventors: Jae-Yeon Jeon, Kyunggi-do (KR); Sang-Ui Choi, Seoul (KR)

(73) Assignee: CERAGEM CO., LTD., Chungcheongnam-Do (KR)

( * ) Notice: Subject to any disclaimer, the term of this patent is extended or adjusted under 35 U.S.C. 154(b) by 134 days.

(21) Appl. No.: 13/807,109

(22) PCT Filed: Jun. 15, 2011

(86) PCT No.: PCT/KR2011/004365
§ 371 (c)(1),
(2), (4) Date: Dec. 27, 2012

(87) PCT Pub. No.: WO2012/002658
PCT Pub. Date: Jan. 5, 2012

(65) Prior Publication Data
US 2013/0110007 A1    May 2, 2013

(30) Foreign Application Priority Data

Jun. 28, 2010  (KR) .................. 10-2010-0061315
May 30, 2011  (KR) .................. 10-2011-0051515

(51) Int. Cl.
*A61B 5/107*  (2006.01)
*A61F 7/00*  (2006.01)
(Continued)

(52) U.S. Cl.
CPC ............ *A61B 5/1072* (2013.01); *A61B 5/4566* (2013.01); *A61B 5/0053* (2013.01);
(Continued)

(58) Field of Classification Search
CPC ...... A61B 5/103; A61B 5/704; A61B 5/1072; A61B 5/1075; A61B 5/4566; A61B 5/0048; A61B 5/0053; A61B 5/0057; A61B 5/4561; A61H 15/02; A61H 23/02; A61H 23/0245; A61H 15/0078; A61H 39/04; A61F 7/00; A61F 7/007; A61F 2007/0024; A61F 2007/0027; A61F 2007/0025; A61F 2007/0056
USPC ..................... 600/594; 601/97–118
See application file for complete search history.

(56) References Cited

U.S. PATENT DOCUMENTS 6,258,047 B1 *  7/2001  Muramatsu ............... 600/594
2008/0097260 A1 *  4/2008  Tsukada et al. ............ 601/98
(Continued)

FOREIGN PATENT DOCUMENTS

CN    1723840        1/2006
JP    H04343846 A   11/1992
(Continued)

OTHER PUBLICATIONS

Machine Translation of KR20-0275399.*
(Continued)

*Primary Examiner* — Devin Henson
*Assistant Examiner* — David J McCrosky
(74) *Attorney, Agent, or Firm* — Michael Best & Friedrich LLP

(57) ABSTRACT

A thermotherapy device having a human body scan function. The device includes a thermo-ceramic unit (110), a transfer motor unit (120) configured to make the thermo-ceramic unit (110) move along a longitudinal direction of a user's backbone, a motor variation generation module (220) configured to measure variations in load of the transfer motor unit (120), and a backbone information generation module (240) configured to generate information about a shape of the user's backbone using data of the motor variation generation module (220).

17 Claims, 12 Drawing Sheets

(51) Int. Cl.
  *A61H 39/04* (2006.01)
  *A61H 15/02* (2006.01)
  *A61B 5/00* (2006.01)
  *A61B 5/103* (2006.01)
  *A61H 15/00* (2006.01)

(52) U.S. Cl.
  CPC ............ *A61B 5/0057* (2013.01); *A61B 5/103* (2013.01); *A61B 5/1075* (2013.01); *A61B 5/4561* (2013.01); *A61B 5/6843* (2013.01); *A61B 5/704* (2013.01); *A61B 2562/0247* (2013.01); *A61F 7/00* (2013.01); *A61F 2007/0024* (2013.01); *A61F 2007/0094* (2013.01); *A61H 15/0078* (2013.01); *A61H 15/02* (2013.01); *A61H 39/04* (2013.01)

(56) References Cited

U.S. PATENT DOCUMENTS

2008/0208080 A1* 8/2008 Ichikawa et al. .............. 600/594
2010/0191088 A1* 7/2010 Anderson et al. .............. 600/594

FOREIGN PATENT DOCUMENTS

| JP | 200421147 | | 7/2006 |
| KR | 1020010007760 | | 2/2001 |
| KR | 1020010044512 | | 6/2001 |
| KR | 200275399 | | 5/2002 |
| KR | 1020020096457 A | * | 12/2002 |
| WO | 02069880 A1 | | 9/2002 |
| WO | WO 02069880 A1 | * | 9/2002 |

OTHER PUBLICATIONS

Machine Translation of KR1020020096457.*
Professional Translation of KR20-0275399.*
Extended European Search Report for Application No. 11801065.1 dated Oct. 8, 2014 (8 pages).

* cited by examiner

Fig. 8
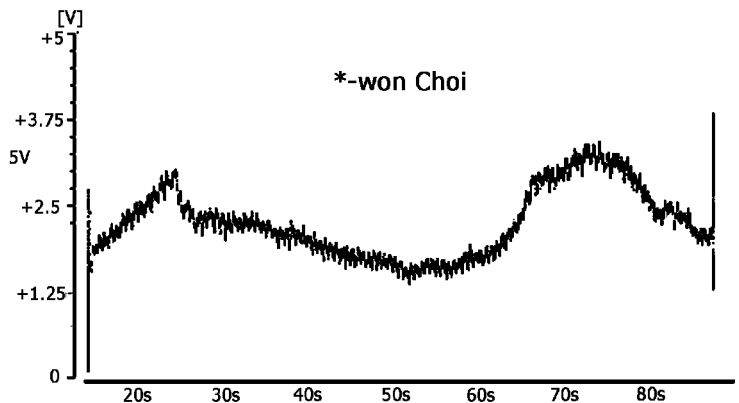
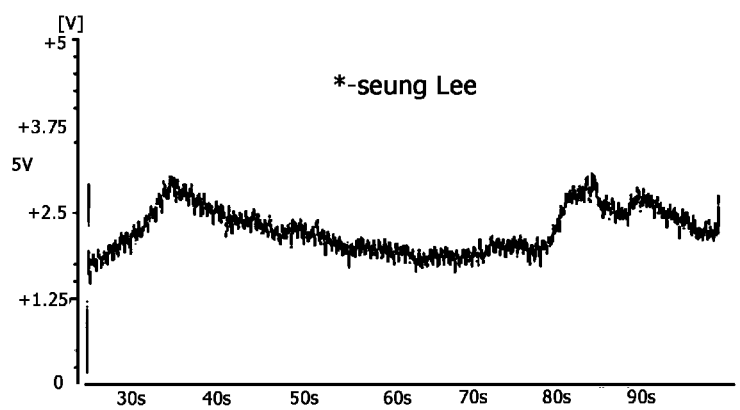
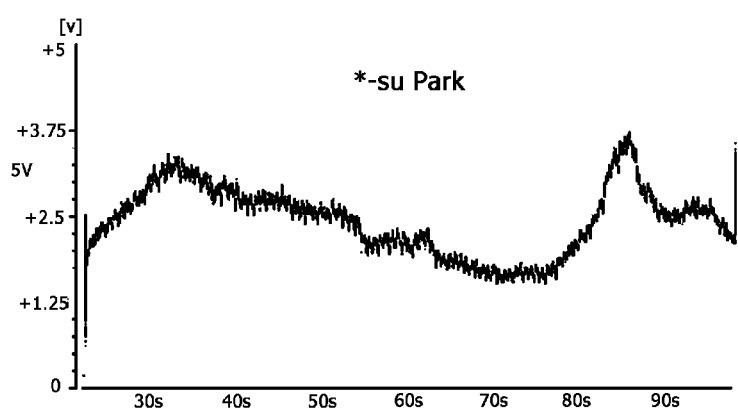

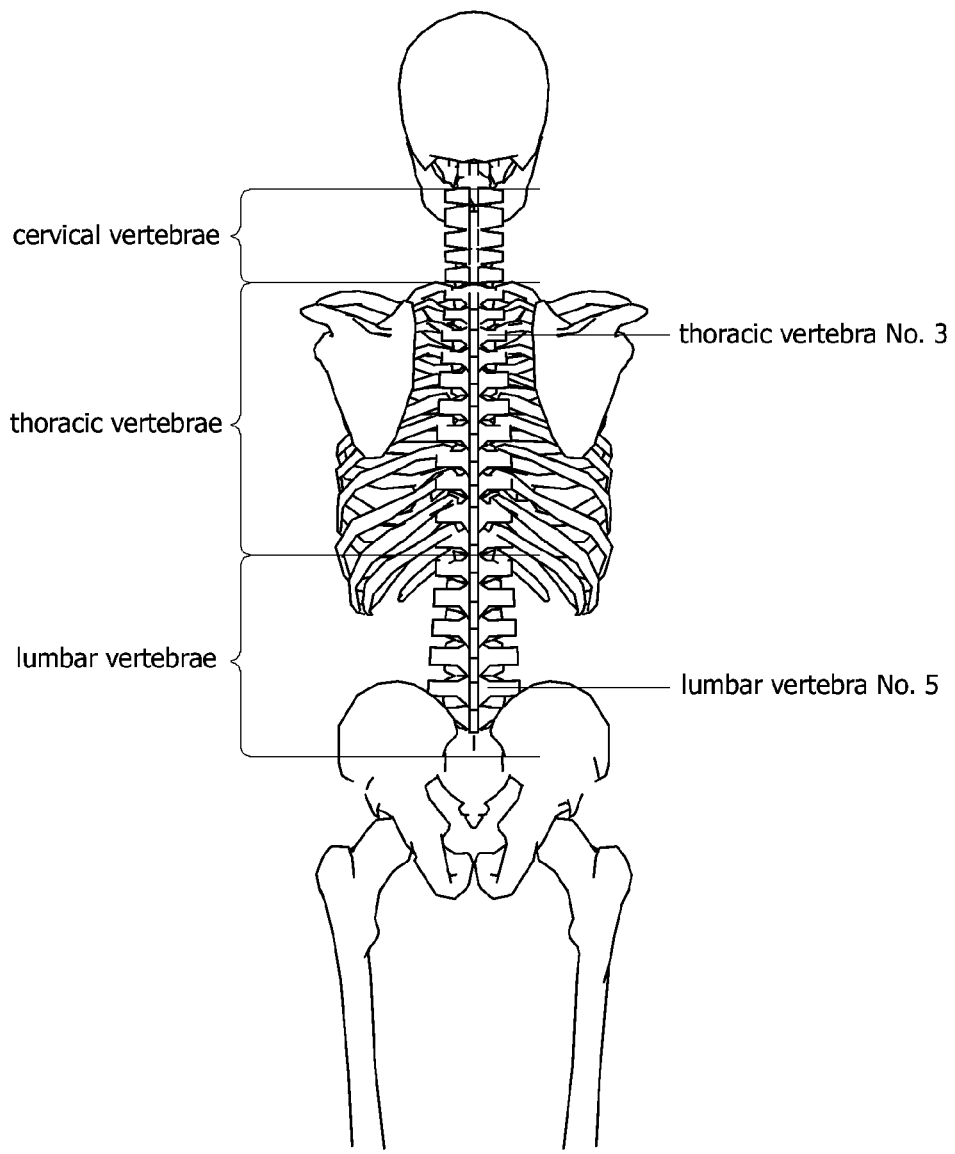

THERMOTHERAPY DEVICE HAVING BODY SCAN FUNCTION AND METHOD FOR SCANNING BODY USING SAME

CROSS-REFERENCE TO RELATED APPLICATIONS

This application is a Section 371 National Phase patent application of International Patent Application No. PCT/KR2011/004365, filed on Jun. 15, 2011, which claims priority to Korean Patent Application No. KR-10-2010-0061315, filed Jun. 28, 2010 and Korean Patent Application No. KR-10-2011-0051515, filed May 30, 2011, the entire contents all of which are hereby incorporated by reference herein.

FIELD OF THE INVENTION

The present invention relates to a thermotherapy device having a human body scan function and a method for scanning a human body using the same. More particularly, the present invention relates to a thermotherapy device having a human body scan function and a method for scanning a human body using the same, which are capable of acquiring necessary information about the shape of a user's backbone by scanning the shape of the user's backbone in advance prior to using the thermotherapy device in actual practice.

BACKGROUND

Thermotherapy devices that are generally used today are bed-type thermotherapy devices that have been developed to maximize the effects of thermal and far-infrared radiation treatment that is applied to users' backbones.

A bed-type thermotherapy device includes a thermo-ceramic unit configured to radiate heat and far-infrared rays onto a user's backbone, a transfer motor configured to reciprocate the thermo-ceramic unit, a curved rail configured to allow the thermo-ceramic unit to make slight vertical movements in response to the curve of the body while the thermo-ceramic unit is reciprocating, and control means configured to electrically control the above elements.

Conventional thermotherapy devices have the problem of being unable to implement the functionality required to make them suitable for individual users because they each adopt a standardized curved rail. The curved rail installed in the bed-type thermotherapy device has a uniform shape and curvature, whereas users who use the thermotherapy device have different body conditions.

Furthermore, the conventional thermotherapy devices have the problem of low utilization because individual body information about the backbone of a user who has unique body conditions is not taken into consideration by the thermotherapy devices.

In order to overcome the above problems, a variety of research that enables users having different body conditions to effectively use a thermotherapy device has been carried out. However, separate devices should be used to measure a user's body conditions. Furthermore, in this case, it is also difficult to accurately measure the curvature of the backbone of a user who lies down on a thermotherapy device, and there is still the problem of preserving and managing the separate devices.

SUMMARY

Accordingly, the present invention has been made keeping in mind the above problems occurring in the prior art, and an object of the present invention is to provide a thermotherapy device having a human body scan function, which is capable of acquiring the length of a user's backbone using data measured by means of conventional elements without additionally installing hardware elements therein.

Another object of the present invention is to provide a thermotherapy device having a human body scan function and a method for scanning a human body using the same, which are capable of processing data about the acquired length of the backbone and providing the fundamental basis of a thermotherapy effect suitable for a user.

In order to accomplish the above objects, the present invention provides a thermotherapy device having a human body scan function, including a thermo-ceramic unit configured to move along a longitudinal direction of a user's backbone; a transfer motor unit configured to move the thermo-ceramic unit; a motor variation generation module configured to measure variations in load of the transfer motor unit; and a backbone information generation module configured to generate information about a shape of the user's backbone using data of the motor variation generation module.

The thermotherapy device may further include an encoder unit configured to count the rpm of the transfer motor; and an encoder variation generation module configured to measure a distance that the thermo-ceramic unit moves using data of the encoder unit.

The backbone information generation module may receive data from the motor variation generation module and the encoder variation generation module, and generate the user's backbone-related information including a length of the user's backbone and a length of each vertebra of the user's backbone.

The measurement of the variations in load of the transfer motor unit may be performed using variations in at least any one of voltage, current and power of the transfer motor.

The motor variation generation module may be a motor data measurement unit configured to measure variations in load of the transfer motor unit via variations in current of the transfer motor; and the motor variation generation module may include a resistance unit configured to convert the variations in current of the transfer motor into variations in voltage variation, and a first analog-to-digital (A/D) conversion unit configured to convert the variations in voltage into digitized data.

The backbone information generation module may be a backbone information calculation unit configured to generate information about the user's backbone; and the backbone information calculation unit may generate the information about the user's backbone using primary information about the user's backbone that is acquired while the thermo-ceramic unit is moving and data entered in a standard backbone information database.

The primary information may be lengths from the user's head to two or more points that are spaced apart on the user's backbone.

If the points are two in number, a first point thereof corresponds to thoracic vertebra No. 3 and a second point thereof corresponds to lumbar vertebra No. 5.

The data entered in the standard backbone information database may be a length of each vertebra with respect to a length of thoracic vertebra No. 3.

The backbone information generation module may include a data operation unit configured to receive data from the motor variation calculation unit and the encoder variation calculation unit, and a data search unit configured to search for information in the data received from the data operation unit, and to transfer the found information to the backbone information calculation unit.

The data operation unit may graph variations in load applied to the transfer motor with respect to variations of the encoder, and transfer the graph to the data search unit.

The data search unit may transfer information found via one or more reflection points of the graph to the backbone information calculation unit.

In order to accomplish the above objects, the present invention provides a human body scan method for a thermotherapy device, including preparation step of inputting user information and making preparation; data measurement step of measuring variations of a transfer motor and variations of an encoder while reciprocating a thermo-ceramic unit; data conversion step of receiving the measured variations and converting the measured variations into data; and backbone information generation step of receiving the resulting data and generating a user's backbone information.

The backbone information generation step may include acquiring primary information about the user's backbone from the received data, and generating information about the user's backbone using the acquired primary information and data entered in a standard backbone information database.

The primary information may be lengths from the user's head to two or more points that are spaced apart on the user's backbone.

If the points are two in number, a first point thereof may correspond to thoracic vertebra No. 3 and a second point thereof may correspond to lumbar vertebra No. 5.

The data entered in the standard backbone information database may be the length of each vertebra with respect to a length of thoracic vertebra No. 3.

The thermotherapy device according to the present invention has the advantage of acquiring basic information about a user's backbone by operating the thermotherapy device in the state in which a user lies on his or her front in such a manner as to use conventional elements without using additional hardware elements.

The thermotherapy device according to the present invention has the advantage of more accurately acquiring information about a user's backbone when utilizing previously entered standard backbone information based on primarily acquired information about the user's backbone.

The thermotherapy device according to the present invention has the advantage of more effectively performing heat fomentation, heat massage and/or thermo-acupressure treatment because the thermotherapy device can scan a user's body at an early stage once or several times, and can then perform thermotherapy based on information about the user's body.

Furthermore, the thermotherapy device according to the present invention has the advantage of providing an additional service for acquiring body information suitable for a user based on information about the user's backbone acquired in the early stage.

Furthermore, the thermotherapy device according to the present invention has the advantage of providing the effect of seeming to use a customized thermotherapy device because the thermotherapy device can provide the most suitable heat fomentation and/or heat massage effects to different users using the single thermotherapy device regardless of the user, thanks to the thermotherapy device being able to anticipate the shape of each user's backbone.

Furthermore, the thermotherapy device according to the present invention has the advantage of providing the effect of seeming to use a customized thermotherapy device to users in or from different countries as well as domestic users because the most suitable standard backbone information can be programmed and applied for each country.

BRIEF DESCRIPTION OF DRAWINGS

The above and other objects, features and other advantages of the present invention will be more clearly understood from the following detailed description taken in conjunction with the accompanying drawings.

FIGS. 7 to 11 are graphs plotting variations in the voltage of a transfer motor that were measured when a bed-type thermotherapy device was used; and FIG. 12 is a schematic diagram of a model of the backbone of the human body.

DETAILED DESCRIPTION

In order to accomplish the above objects, the present invention provides a thermotherapy device having a human body scan function, including a thermo-ceramic unit configured to move along a longitudinal direction of a user's backbone; a transfer motor unit configured to move the thermo-ceramic unit; a motor variation generation module configured to measure variations in load of the transfer motor unit; and a backbone information generation module configured to generate information about a shape of the user's backbone using data of the motor variation generation module.

Preferred embodiments of the present invention will be described in detail below with reference to exemplary drawings. However, it will be apparent that the accompanying drawings are intended to more fully describe the technical spirit of the present embodiment and the technical spirit of the present embodiment is not limited thereto. It is noted that this embodiment is a preferred embodiment and takes into consideration a bed-type thermotherapy device as an example.

This embodiment effectively improves a method for using the thermotherapy device by using existing elements without newly installing additional hardware elements in the thermotherapy device. Accordingly, this embodiment may be described based on the elements of a typical thermotherapy device.

Figure 1:
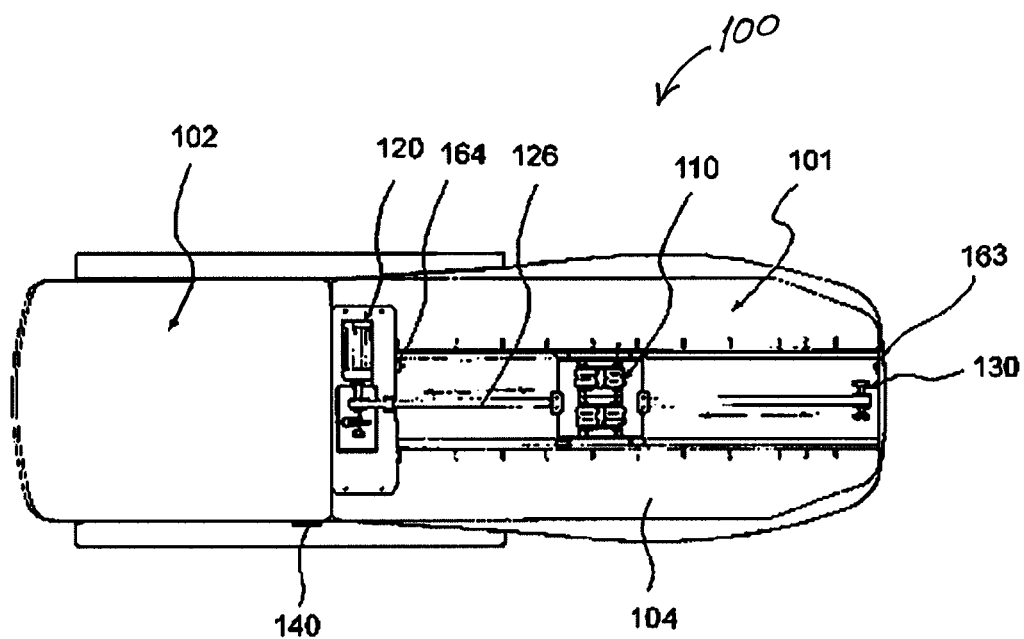
FIG. 1 is a plan view schematically showing the internal configuration of a bed-type thermotherapy device.
Figure 2:
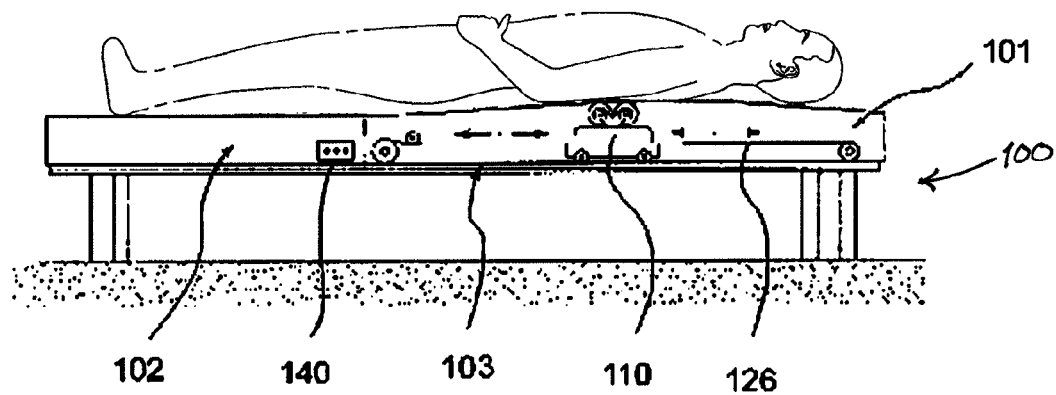
FIG. 2 is a schematic side view in which the bed-type thermotherapy device is viewed from a side thereof.

FIG. 1 is a plan view schematically showing the internal configuration of a bed-type thermotherapy device, and FIG. 2 is a schematic side view in which the bed-type thermotherapy device is viewed from a side thereof.

Figure 3:
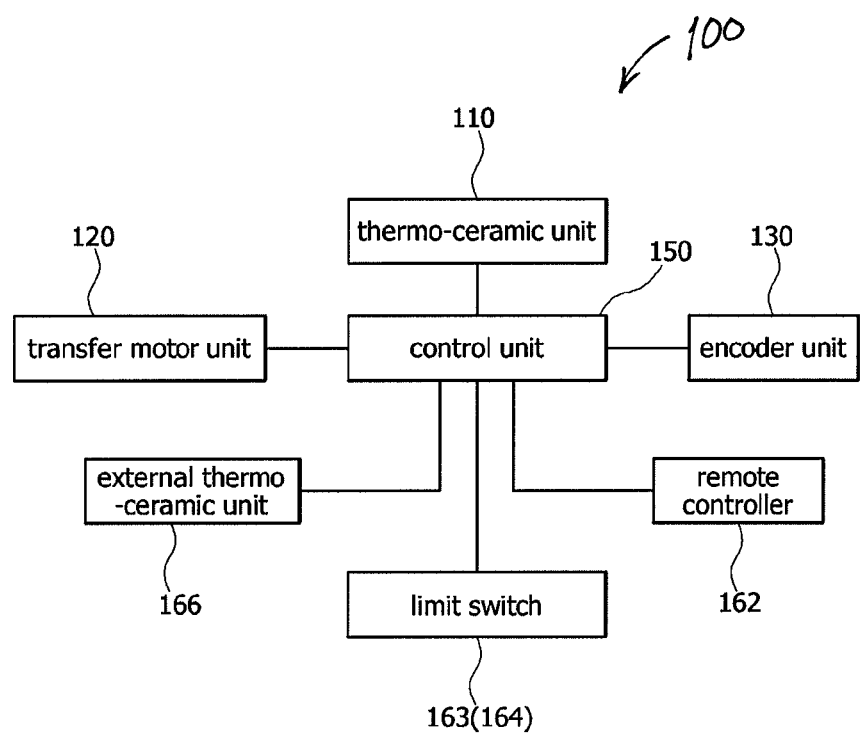
FIG. 3 is a block diagram schematically showing the elements of the thermotherapy device according to the present invention.

FIG. 3 is a block diagram schematically showing the elements of the thermotherapy device according to the present invention.

Figure 4:
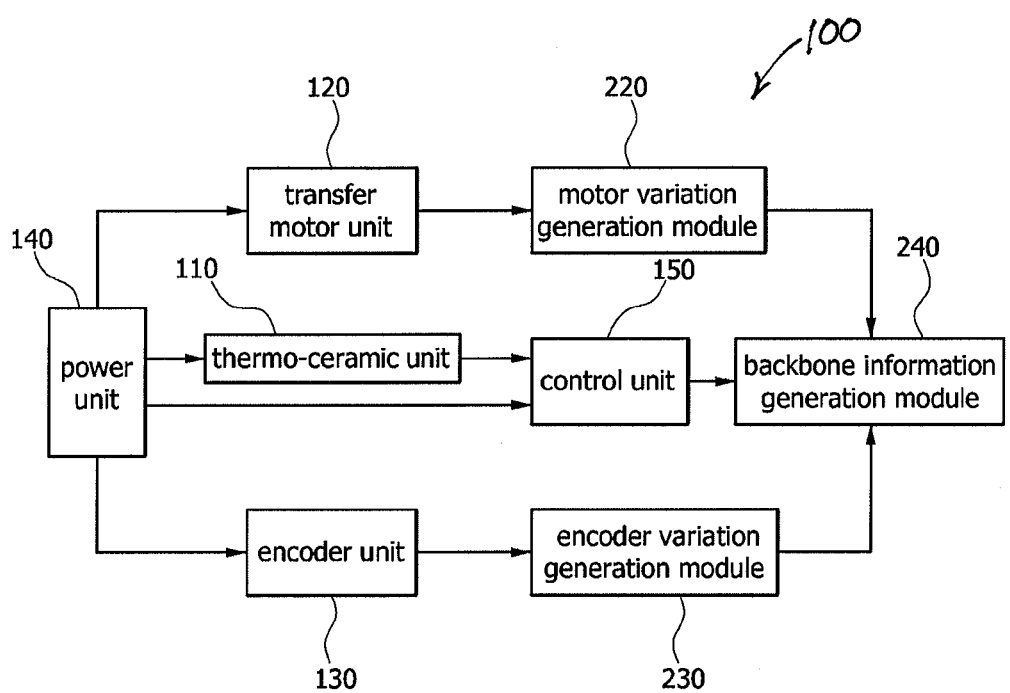
FIG. 4 is a schematic block diagram illustrating the principal parts of the thermotherapy device according to the present invention.
Figure 5:
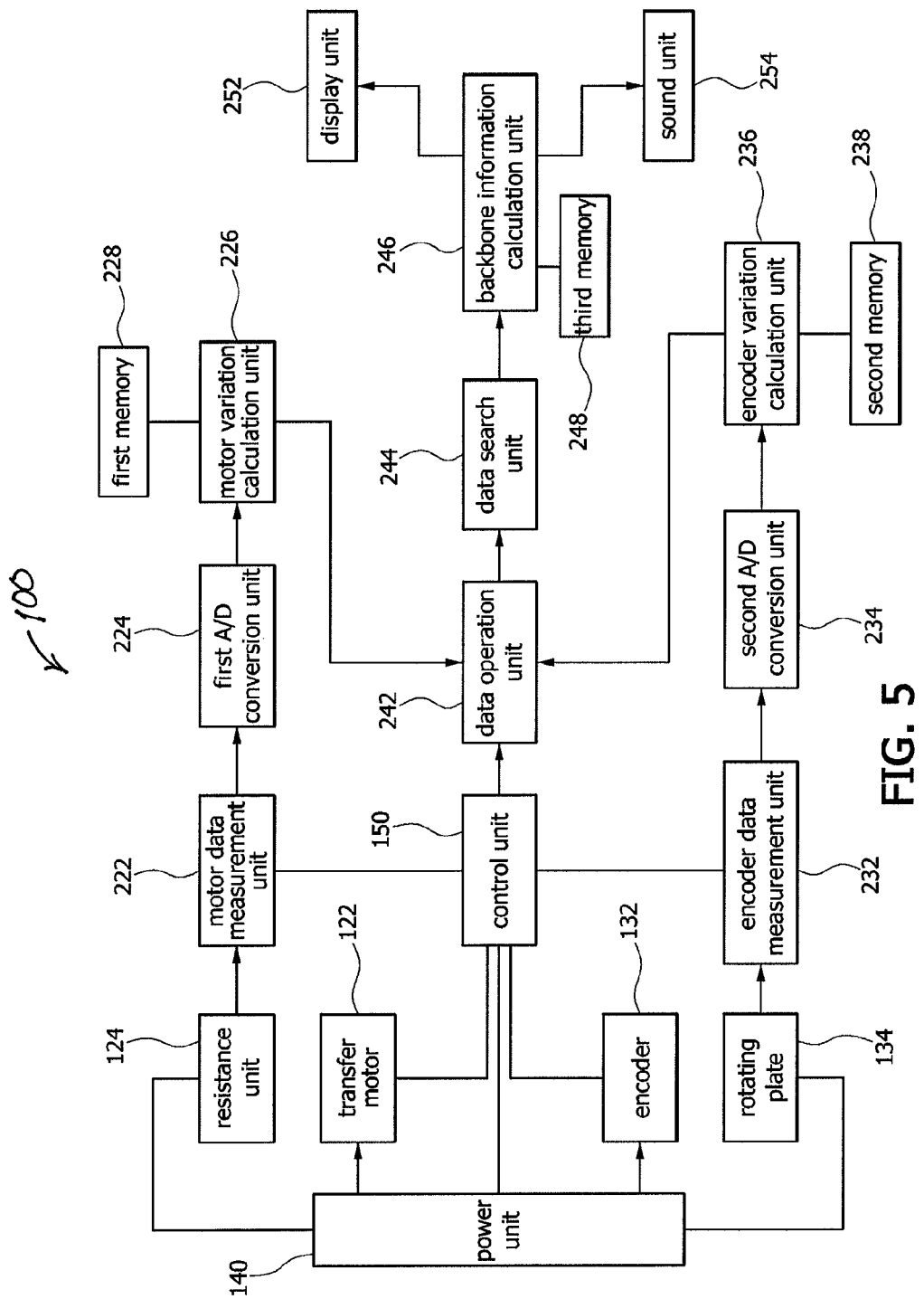
FIG. 5 is a detailed block diagram illustrating the principal parts of the thermotherapy device according to the present invention in greater detail.

FIG. 4 is a schematic block diagram illustrating the principal parts of the thermotherapy device according to the present invention, and FIG. 5 is a detailed block diagram illustrating the principal parts of the thermotherapy device according to the present invention in greater detail.

A thermotherapy device 100 basically includes a main mat 101 intended for a user's upper body and backbone and an auxiliary mat 102 intended for the user's lower body. Furthermore, a support part 103 for supporting the main mat and the auxiliary mat thereon may be further included as desired.

The main mat 101 includes a body part 104 that is configured to support the user's upper body. The body part 104 is fabricated in the shape of a plate in which a longitudinal groove is formed at the center thereof.

The thermotherapy device 100 includes a thermo-ceramic unit 110 so as to provide heat fomentation and heat massage effects to the user's body part (in particular, the user's back portion) while moving in the direction of the user's backbone. The thermo-ceramic unit 110 is installed inside the longitudinal groove. Furthermore, the thermo-ceramic unit 110 includes a heating unit that generates high-temperature heat and far-infrared rays using electrical energy that is supplied by a power unit 140.

The thermo-ceramic unit 110 provides heat fomentation and heat massage effects to the user using high-temperature heat and far-infrared rays that are generated by the heating unit. The thermo-ceramic unit 110 may include either a cap-type heating unit or a roller-type heating unit depending on the shape thereof.

The shape of the heating unit is not limited thereto, but may have any of a variety of shapes and structures. The heating unit includes a heat generation part configured to generate heat using electrical energy and a heat radiation part configured to be heated by the heat generation part. In this embodiment, a lamp or an electric heater is used as the heat generation part, and a far-infrared radiator such as jade is used as the heat radiation part. However, the heat generation part and the heat radiation part are not limited thereto, and a variety of heat generators or a variety of materials and substances that can be heated by heat may be used.

The thermotherapy device 100 includes a transfer motor unit 120 so that the thermo-ceramic unit 110 can reciprocate inside the body part 104. The transfer motor unit 120 includes a transfer motor 122 configured to be supplied with electrical energy and be rotated, and transfer means 126 connected to the transfer motor 122 and configured to transfer rotating force as the transfer motor 122 is rotated. The transfer means 126 is coupled to the thermo-ceramic unit 110, and is used to transfer the thermo-ceramic unit 110 in a forward or backward direction (that is, in one direction or in the opposite direction) in response to the forward or reverse rotation of the transfer motor 122. One that is selected from among a transfer belt, a transfer chain, and a transfer rope may be used as the transfer means 126. It is apparent that the transfer means 126 is not limited thereto but one of a variety of means for transferring an object using the driving force of a motor may be used as the transfer means 126.

The thermotherapy device 100 includes an encoder unit 130 that measures and controls the operation of the transfer motor 122 and the distance which the thermo-ceramic unit 110 moves. The encoder unit 130 can accurately measure the distance which the thermo-ceramic unit 110 moves by accurately checking the rpm of the transfer motor 122. The encoder unit 130 includes an encoder 132, a sensor, and a sensing through hole. It is preferable to include a rotating plate 134 which is connected to the encoder 132 and in which a plurality of sensing parts is formed to calculate the distance which the thermo-ceramic unit 110 is transferred. It is preferable that the sensing parts be fabricated in the form of sensing through holes that are capable of sensing the rotation of the rotating plate 134 using the sensors. It is apparent that the encoder unit 130 is not limited thereto but a variety of types of motor encoders may be used.

The thermotherapy device 100 includes a control unit 150 configured to control the operation of the thermotherapy device, and a remote controller 162 configured to receive the user's manipulation signals and provide the signals to the control unit 150. The control unit 150 controls the times, ranges and periods of the various types of parts of the thermotherapy device, and operates or stops the operations of the various types of parts according to previously programmed, input information. In this embodiment, the control unit 150 may be a single control chip or device or a plurality of control chips or devices that are mounted on a single PCB or a plurality of PCBs.

The remote controller 162 may be held by the user, and is used to input necessary information. Here, the remote controller 162 may have any of a variety of wired or wireless structures.

The thermotherapy device 100 may include a limit switch 164 that enables the thermo-ceramic unit 110 to automatically switch its moving direction and then move when the thermo-ceramic unit 110 reaches an end of the body part 104 while moving inside the body part 104. The limit switch 164 is a kind of changeover switch, and is divided into an upper end switch and a lower end switch (see FIG. 1) and installed in order to switch the rotation direction of the transfer motor 110.

Furthermore, the bed-type thermotherapy device may include a separate external thermo-ceramic unit 166 in addition to the thermo-ceramic unit 110. The external thermo-ceramic unit 166 may be one of a 3-hole thermo-ceramic unit, a 6-hole thermo-ceramic unit, a 9-hole thermo-ceramic unit, and a 12-hole thermo-ceramic unit. Furthermore, the bed-type thermotherapy device includes a fabric covering (not shown) that entirely surrounds the body part 104 and prevents the thermo-ceramic unit 110 from directly coming into contact with the user's body part.

The thermotherapy device 100 of this embodiment may scan the shape of the user's backbone using the load of the transfer motor 122 attributable to the movement of the thermo-ceramic unit 110, as described above.

For this purpose, the thermotherapy device 100 according to this embodiment includes a motor variation generation module 220 configured to measure the variation of the transfer motor 122 during the operation of the transfer motor unit 120 and to process the variation using a control signal of the control unit 150, an encoder variation generation module 230 configured to measure the variation of the encoder 132 during the operation of the encoder unit 130 and to process the variation using a control signal of the control unit 150, and a backbone information generation module 240 configured to generate information about the user's backbone necessary for the functionality of the thermotherapy device in response to a control signal of the control unit 150 based on a data value provided by the motor variation generation module 220 and a data value provided by the encoder variation generation module 230.

The above-described modules may be fabricated in the form of separate hardware configurations, or may be provided in the form of programs embedded in separate chips. It is apparent that part of each module may be provided in the form of a hardware configuration and the remaining part of the module may be provided in the form of a program. This will be described in detail in the following description.

In this embodiment, the motor variation generation module 220 measures the load variation of the transfer motor unit 120 during the operation of the transfer motor unit 120, and calculates load variation in real time based on the measured load variation. The motor variation generation module 220 includes a motor data measurement unit 222, a first A/D conversion unit 224, and a motor variation calculation unit 226.

The motor data measurement unit 222 measures variation in load that is applied to the transfer motor 122. The load variation of the transfer motor 122 may be measured using at least any one of the rpm of the transfer motor 122, the amount of current supplied to the transfer motor 122, and the value of voltage supplied to the transfer motor 122.

The motor data measurement unit 222 may be provided with a separate resistance unit 124. That is, in the case where the load of the transfer motor 122 varies while fixed voltage is being applied to the transfer motor 122, the amount of current of the transfer motor 122 varies. In this case, this embodiment converts variation in current into a voltage value using the separate resistance unit 124 in order to measure the current variation of the transfer motor 122, and uses the resulting data as data about the load variation of the transfer motor 122. It is apparent that this embodiment is not limited thereto but it may be possible to measure the voltage variation of the transfer motor 122 attributable to load and to use the measure voltage variation as data about the load variation of the transfer motor 122.

The first A/D conversion unit 224 converts analog data measured by the motor data measurement unit 222 into digital data. The control unit 150 sends the analog data about motor load measured by the motor data measurement unit 222 to the first A/D conversion unit 224. The first A/D conversion unit 224 converts input analog data into digital data.

The motor variation calculation unit 226 converts the digitized load data of the transfer motor 122 into a real-time data value. The control unit 150 inputs the digital data supplied by the first A/D conversion unit 224 to the motor variation calculation unit 226. The motor variation calculation unit 226 converts the input digital data into data per preset unit time. The preset unit time may be set to 1/tens of seconds to several seconds. There is an advantage in that more accurate data can be obtained in inverse proportion to the size of the preset unit time. The control unit 150 supplies the calculated data per unit time obtained by the motor variation calculation unit 226 to the backbone information generation module 240. In greater detail, it inputs the data to the data operation unit 242. It is preferable to first store the calculated data per unit time in first memory 228 and then input the data to the data operation unit 242.

In this embodiment, the encoder variation generation module 230 measures the variation of the encoder unit 130 during the operation of the encoder unit 130, and calculates the variation in real time based on the measured variation.

The encoder variation generation module 230 includes an encoder data measurement unit 232, a second A/D conversion unit 234, and an encoder variation calculation unit 236.

The encoder data measurement unit 232 measures the variation of the encoder 132. The variation of the encoder 132 may be measured using the rpm of the rotating plate 134 provided in the encoder 132. It is most preferable to check the number of clicks of through holes that varies as the rotating plate 134 rotates. The reason for this is that when the number of clicks of sensing through holes formed in the rotating plate 134 is measured, the distance that the thermo-ceramic unit 110 moves can be easily determined.

The second A/D converter 234 converts analog data into digital data. The control unit 150 sends the analog data measured by the encoder data measurement unit 232 to the second A/D converter 234. The second A/D converter 234 converts the input analog data into digital data.

The encoder variation calculation unit 236 converts the digitized data of the encoder 132 into a real-time data value. The control unit 150 inputs the digital data supplied by the second A/D converter 234 to the encoder variation calculation unit 236. The encoder variation calculation unit 236 converts the input digital data into data per preset unit time. The preset unit time may be set to a value from 1/tens of seconds to 1/several seconds. There is an advantage in that more accurate data can be obtained in inverse proportion to the size of the preset unit time. The control unit 150 supplies the calculated data per unit time obtained by the encoder variation calculation unit 236 to the backbone information generation module 240 and, in greater detail, inputs the data to the data operation unit 242. It is preferable to first store the calculated data per unit time in second memory 238 and then input the data to the data operation unit 242.

In this embodiment, the backbone information generation module 240 calculates data values about the user's backbone necessary for the functionality of the thermotherapy device based on a data value provided by the motor variation generation module 220 and a data value provided by the encoder variation generation module 230. The backbone information generation module 240 may scan the shape of the backbone using the load variation of the transfer motor 122. Furthermore, since the backbone information generation module 240 is based on the variation of the encoder 132, it generates the user's backbone information related to the distance that the thermo-ceramic unit 110 moves inside the thermotherapy device 100. The user's backbone information includes at least any one piece of information of the expected length of the user's backbone, the length of each vertebra of the user's backbone, the curvature of the user's backbone, the relative location of the user's backbone, the relative location of each vertebra of the user's backbone, and the height calculated based on the user's backbone.

The backbone information generation module 240 includes a data operation unit 242, a data search unit 244, and a backbone information calculation unit 246.

The data operation unit 242 is provided with motor-related data supplied by the motor variation calculation unit 226 and encoder-related data supplied by the encoder variation calculation unit 236. Thereafter, the motor-related data and the encoder-related data are combined together and an operation is performed on them. The data operation unit 242 graphs variation in load applied to the transfer motor 122 in relation to the variation of the encoder 132. It is apparent that this embodiment is not limited thereto but it may be possible to graph data about the load variation of the transfer motor 122.

The control unit 150 inputs the data graphed by the data operation unit 242 to the data search unit 244, which corresponds to a subsequent stage.

The data search unit 244 searches for necessary information based on data input by the data operation unit 242. The data search unit 244 searches for necessary information according to program information preset by the control unit 150 for a preset time based on the data input by the data operation unit 242 in real time. The set program information may be input in various ways. For example, when the data search unit 244 searches for the highest variation of data for a preset time, the set program information may be searched for by detecting the highest variation per unit time or by detecting the highest variation per preset time. Furthermore, when the data search unit 244 searches for the reflection point of data variation for a preset time, the set program information may be searched for by detecting the reflection point of variation per unit time or by detecting the reflection point of variation per preset time. When the data search unit 244 searches for a specific set value for a preset time, the specific value may be input in advance and then searched for. Here, the unit time may be based on 1 second, and the preset time may be based on any one selected from among the time of the variation of one click, the time for which the thermo-ceramic unit 110 moves inside the thermotherapy device once, the time for which the thermo-ceramic unit 110 reciprocates inside the thermotherapy device once, and the time for which the thermo-ceramic unit 110 reciprocates inside the thermotherapy device two or four times. When the user desires to obtain his or her body information, particularly backbone information, prior to applying heat fomentation and heat massage to his or her body using the thermotherapy device, and then apply heat fomentation based on the backbone information, it is preferable to obtain information about his or her own backbone while moving the thermo-ceramic unit 110 from the head to the buttocks at least one time while the user is lying on his or her front. The data search unit 244 generates a varying data value depending on a preset program or a preset condition. A preferred embodiment illustrates a case in which data about thoracic vertebra No. 3 and data about lumbar vertebra No. 5 related to the user's backbone are obtained using the reflection point of the highest variation while the thermo-ceramic unit 110 is moving inside the thermotherapy device in one direction or is reciprocating once or several times. The control unit 150 inputs the data generated by the data search unit 244 to the backbone information calculation unit 246, which corresponds to a subsequent stage.

The backbone information calculation unit 246 of the backbone information generation module 240 infers and generates the user's backbone information based on the data input by the data search unit 244. The backbone information calculation unit 246 functions to calculate information about the user's backbone (primary information) using the motor-related data and the encoder-related data while the thermo-ceramic unit 110 is moving inside the thermotherapy device in one direction or is reciprocating once or several times in the state in which the user lies on his or her front. It is preferred that the backbone information calculation unit 246 infers information about the user's backbone (secondary information) based on the data input by the data search unit 244, as contrasted with a standard backbone information database.

Data entered in the standard backbone information database may be created by setting a specific population and measuring information about the backbones of all members that constitute the population, or may be created using information previously created and used by a nation or a public organization in advance. The standard backbone information may be categorized by region, age and/or gender. Categorization by region may include categorization by country and by continent. Since final calculated values vary depending on how to acquire and use the standard backbone information, the acquisition and use of the information are both very important.

The primary information is characterized in that it is based on the lengths from the user's head to two or more points spaced apart along the user's backbone. That is, these points may be arbitrary points located along the user's backbone, and the primary information may be the distances from the user's head to the points.

It is preferred that when the points are two in number, a first point correspond to thoracic vertebra No. 3 and a second point correspond to lumbar vertebra No. 5.

A method by which the backbone information calculation unit 246 acquires the user's backbone information using data entered in the standard backbone information database will now be introduced as an example. The case in which the backbone information calculation unit 246 acquires data about the user's thoracic vertebra No. 3 and data about the user's lumbar vertebra No. 5 will be described. When the standard backbone information relates to a Korean adult's standard backbone data, the backbone information calculation unit 246 obtains relative information about the user's backbone based on an average Korean backbone by comparing the data about thoracic vertebra No. 3 and the data about lumbar vertebra No. 5 with a Korean adult's standard backbone data. If the standard backbone information relates to data about the standard backbone of a Korean male in his 30s, the backbone information calculation unit 246 can acquire more accurate relative information about the user's backbone by contrasting the data about thoracic vertebra No. 3 and the data about lumbar vertebra No. 5 with the data about the standard backbone of a Korean male in his 30s. If the standard backbone information relates to data about the standard backbone of a Korean female in her 50s, the backbone information calculation unit 246 can acquire more accurate relative information about the user's backbone based on the standard backbone of the female in her 50s by contrasting the data about thoracic vertebra No. 3 and the data about lumbar vertebra No. 5 with the data about the standard backbone of the Korean female in her 50s. Accordingly, when the user inputs user information, such as his or her age, birth place or birth country, to the remote controller 162, the control unit 150 selects corresponding standard backbone information, and the backbone information calculation unit 246 automatically infers and creates the user's backbone information. It is preferred that the user's backbone information be first stored in the third memory 248 and then processing proceeds to a subsequent stage.

Once the thermotherapy device 100 according to this embodiment has obtained the user's backbone information through the above-described process, it may be utilized based on the backbone information in a variety of ways. For example, the user's backbone information may be visually represented by displaying it on a display unit 252, or may be aurally represented by playing the user's backbone information via a sound unit 254.

Furthermore, it may be possible to create a model of the user's backbone using the user's backbone information, to determine the shape of a curved rail along the created model, and to allow the thermo-ceramic unit 110 to reciprocate along the curved rail. Furthermore, the user may specify the portion of his or her backbone requiring more intensive thermotherapy, and may apply heat fomentation and heat massage to the portion using the thermo-ceramic unit 110.

Furthermore, this embodiment provides a method for scanning a human body using the human body scan device.

This embodiment provides a foundation on which it may be possible to create the user's backbone information through the following series of steps and to utilize the thermotherapy device using the backbone information in a variety of ways.

Figure 6:
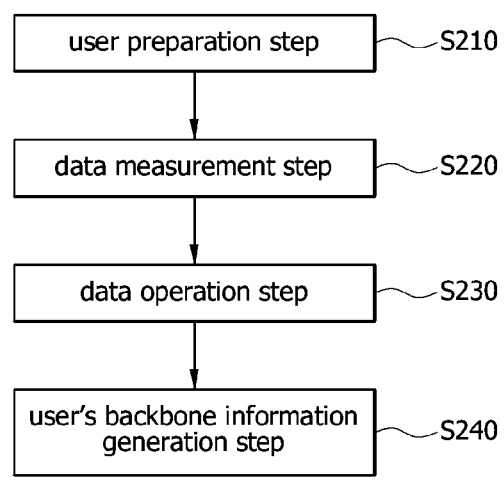
FIG. 6 is a flow diagram schematically introducing a method of using the thermotherapy device according to the present invention.
Figure 7:
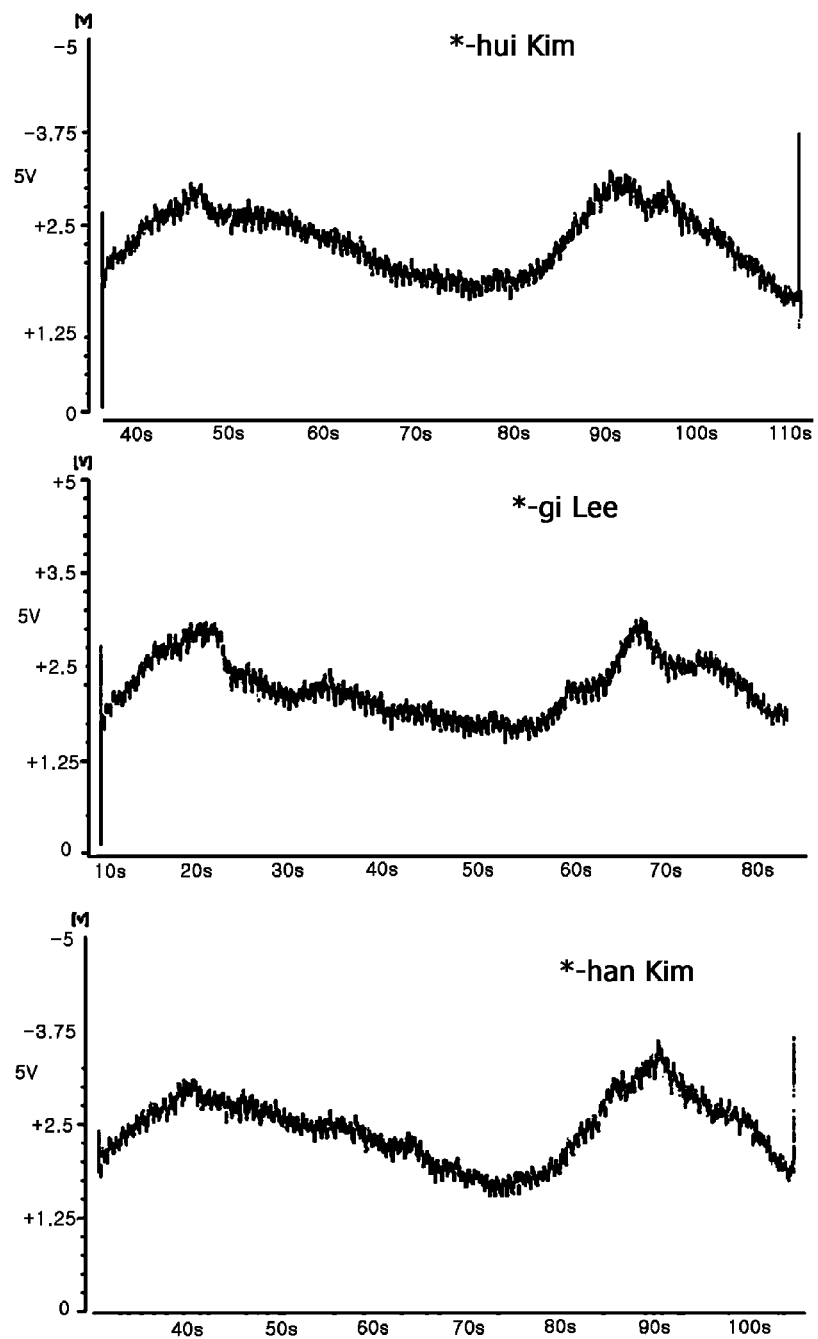
Figure 9:
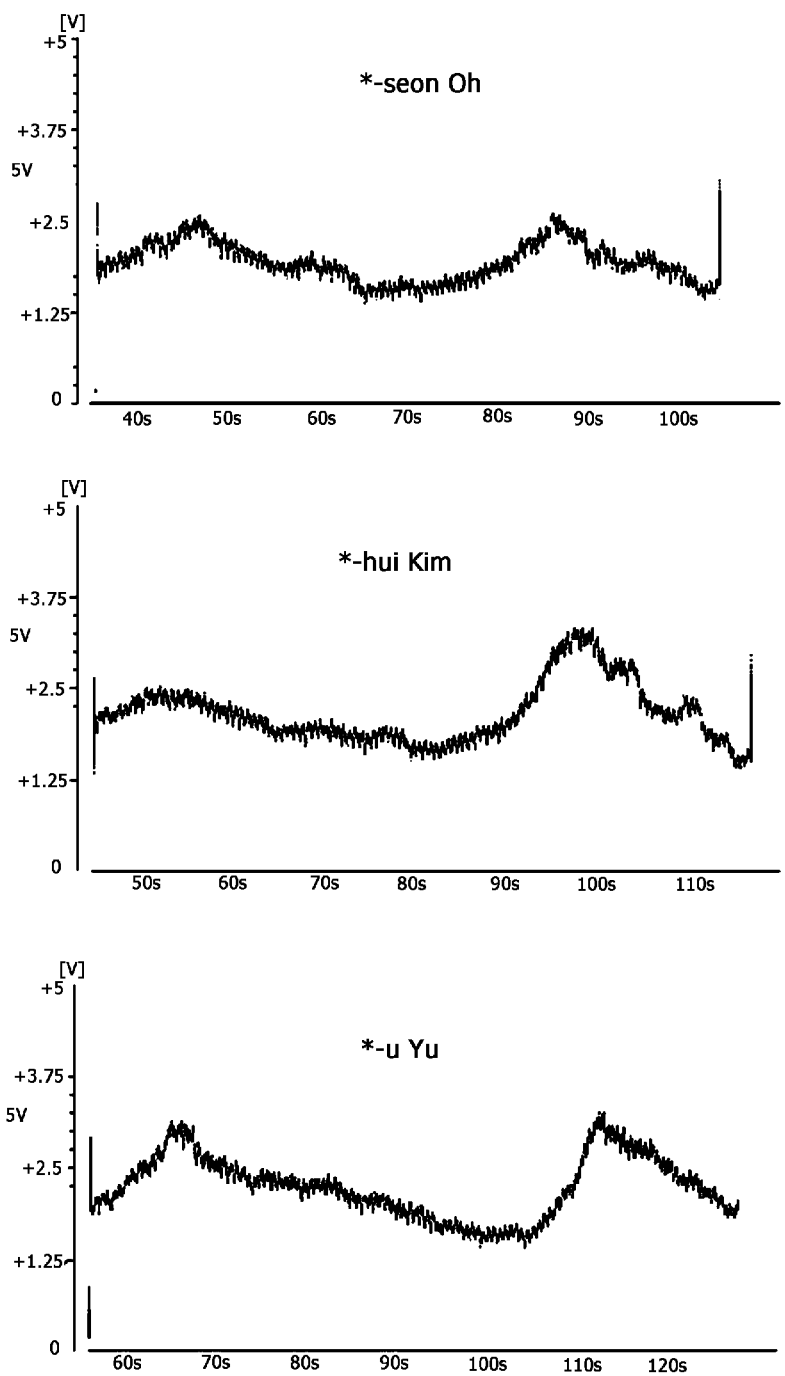
Figure 10:
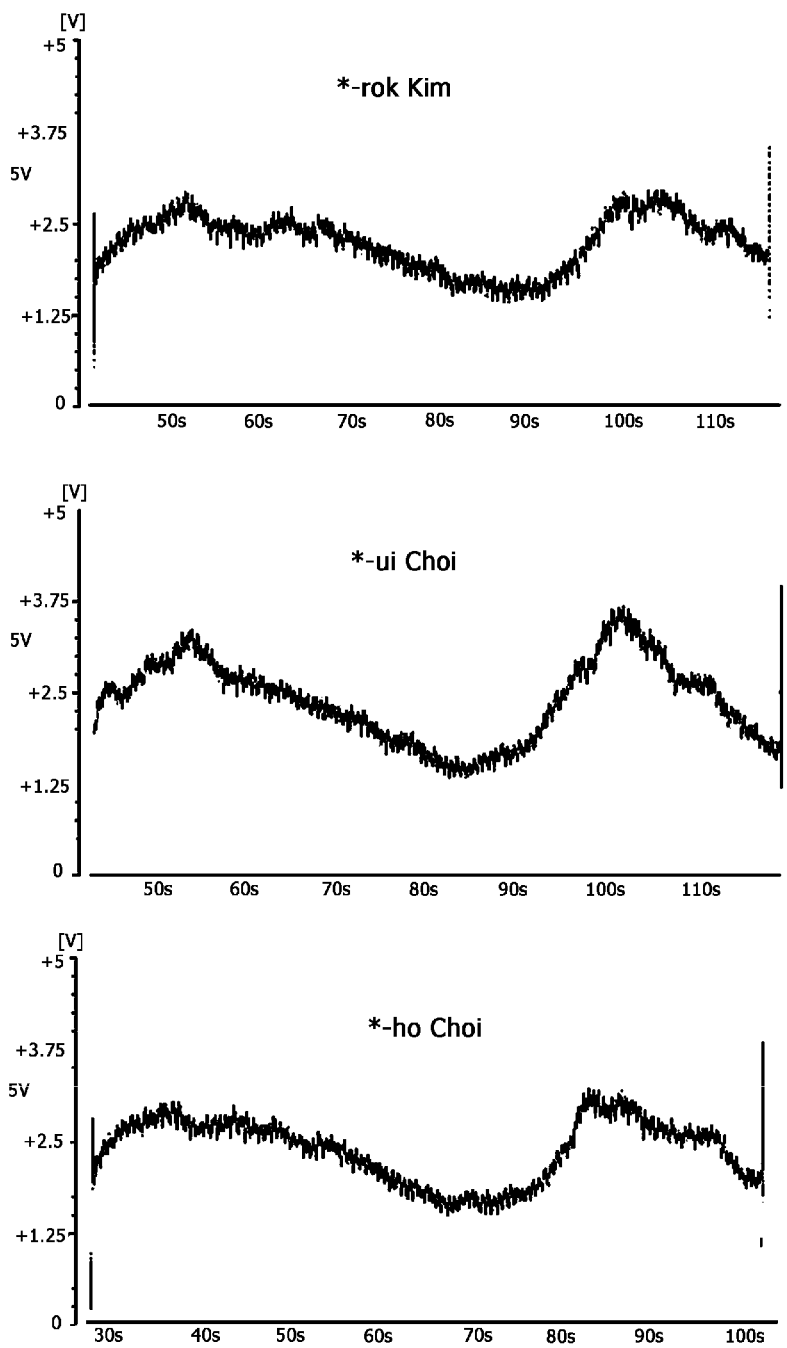
Figure 11:
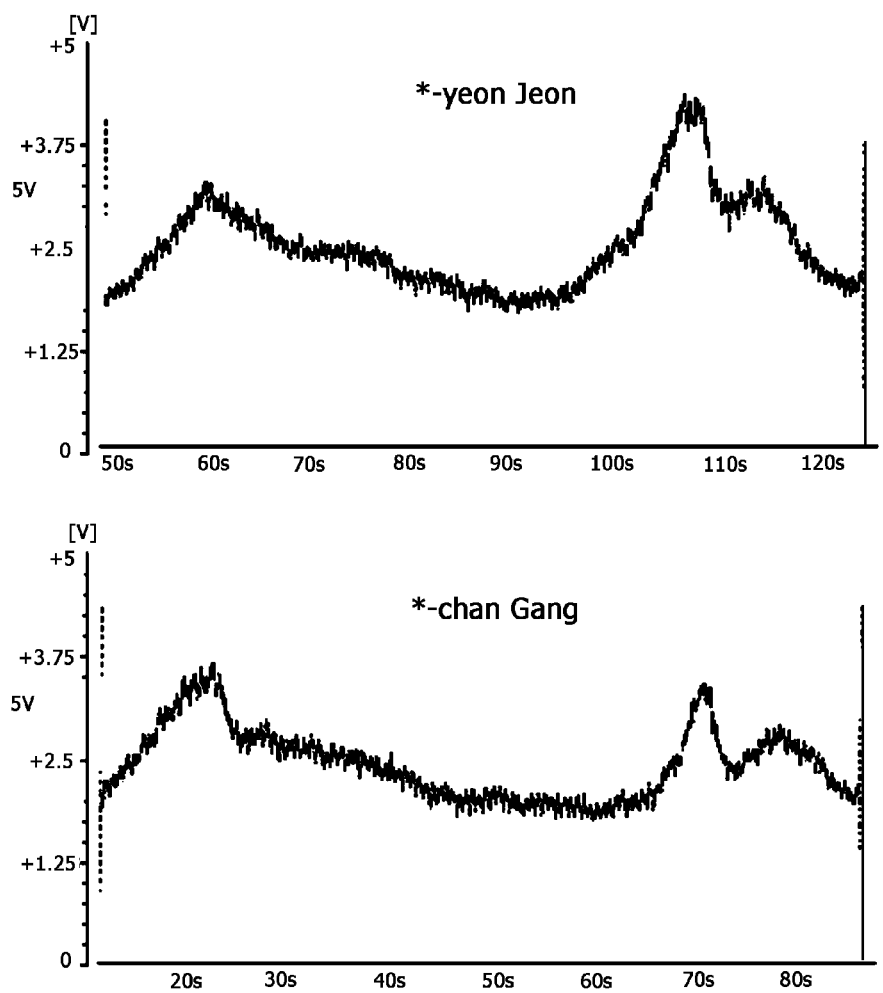

FIG. 6 is a block diagram schematically introducing a method of using the thermotherapy device 100 according to this embodiment.

1). User Preparation Step (S210):

This embodiment includes user preparation step S210 of inputting and preparing information using separate input means, including the remote controller 162, while the user is lying down on the thermotherapy device.

In this embodiment, the user may input his or her predetermined information in advance using the remote controller 162 while lying down on the thermotherapy device 100. If the thermotherapy device is a bed-type thermotherapy device or a mat-type thermotherapy device, it is preferred that the user lie down; if the thermotherapy device is a seat-type thermotherapy device, it is preferred that the user comfortably lean on a backrest (not shown). Here, the above-described predetermined information includes the user's nationality, gender or age group. If necessary, the user's height or weight may be added. The reason for inputting predetermined information using the remote controller 162 is to perform required operations or processing in connection with information stored in the thermotherapy device using the information. When the user inputs necessary information and operates the thermotherapy device 100 using the remote controller 162, the thermo-ceramic unit 110 gradually starts to move from one end of the main mat 101 opposite the auxiliary mat 102 toward the auxiliary mat 102.

It is apparent that the user information may not be input as desired. That is, when the user selects an automatic mode, scan and treat tasks may be performed without the input of user information.

In this embodiment, according to the information input by the user, optimum information suitable for the information is selected. When the user inputs information about his or her nationality, age and gender to the thermotherapy device 100, this embodiment selects and specifies standard backbone information most suitable for the input information. For example, when the user inputs a Korean male 43 years old, this embodiment selects and specifies information about the standard backbone of a Korean male in his 40s, the information about the standard backbone of a Korean male in his 40s may be usefully used in the following data operation step.

2). Data Measurement Step (S220):

This embodiment includes data measurement step S220 of measuring the variation of the transfer motor 122 and the variation in the number of clicks of the encoder rotating plate 134 while moving the thermo-ceramic unit 110 in one direction once or reciprocating the thermo-ceramic unit 110 once or several times in the state in which the user lies down on the thermotherapy device.

In this embodiment, the user operates the thermo-ceramic unit 110 using the remote controller 162 in the state in which the user lies down on the thermotherapy device 100. The control unit 150 rotates the transfer motor 122 in a forward direction, and accordingly the thermo-ceramic unit 110 gradually starts to move from the upper end limit switch 163 in a central direction. At the same time, the encoder 132 starts to operate, and the rotating plate 134 gradually starts to rotate.

In this case, the load value of the transfer motor 122 that moves the thermo-ceramic unit 110 may be varied by the weight of the user.

If the weight of the user is high, the pressure applied to the thermo-ceramic unit 110 becomes higher, and therefore the force received by the thermo-ceramic unit 110 increases. Furthermore, the load value thereof increases. In contrast, if the weight of the user is relatively low, the pressure applied to the thermo-ceramic unit 110 becomes relatively low, and therefore force received by the thermo-ceramic unit 110 decreases. The load value thereof tends to decrease. However, since the weight of the user acts in the direction perpendicular to the direction in which the thermo-ceramic unit 110 moves, it does not significantly influence the movement of the thermo-ceramic unit 110.

Furthermore, the load value of the transfer motor 122 may be varied by the shape of the user's backbone.

The thermo-ceramic unit 110 is considerably influenced by the shape of the user's backbone in the direction in which it moves. The reason for this is that the shapes of users' backbones do not extend straight along a rectilinear line but are slightly curved in the form of letter S. While the thermo-ceramic unit 110 is moving inside the thermotherapy device, part of the thermo-ceramic unit 110 experiences high resistance (load) and part of the thermo-ceramic unit 110 experiences low resistance depending on the shape of the user's backbone, and the variation in resistance results in variation in load applied to the transfer motor 122.

Accordingly, if the rpm of the transfer motor 122, the amount of current applied to the transfer motor 122, and the value of voltage supplied to the transfer motor 122 are measured and the variations in the measured values are calculated, information from which the shape of the user's backbone can be inferred may be obtained. In this embodiment, the variation in load applied to the transfer motor 122 is measured using the motor data measurement unit 222. As described above, when the thermo-ceramic unit 110 is moved by applying a specific amount of voltage to the transfer motor 122, the amount of current of the transfer motor 122 is varied by the shape of the backbone. Here, the variation in current directly becomes a load value. Here, the separate resistance unit 124 is provided to detect variation in the amount of current, detects the variation in the amount of current as variation in voltage, and provides the variation in voltage to the control unit and the backbone information generation module in the form of digitized data.

Meanwhile, in this embodiment, the distance that the thermo-ceramic unit 110 moves is measured using the rpm of the rotating plate 134 provided in the encoder 132. The plurality of sensing through holes (not shown) is formed through the rotating plate 134, and the encoder data measurement unit 232 measures the distance that the thermo-ceramic unit 110 moves by counting the number of clicks of the sensing through holes.

3). Data Conversion Step (S230):

This embodiment includes data conversion step S230 of receiving the data measured during the movement of the thermo-ceramic unit 110 when the user lies down on the thermotherapy device and converting the received data into real-time data.

In this embodiment, the motor data measurement unit 222 measures variation in the resistor 124 of the transfer motor 122, and the first A/D conversion unit 224 converts the variation into digital data. The resulting digital data is calculated as real-time variation data by the motor variation calculation unit 226.

Furthermore, in this embodiment, the encoder data measurement unit 232 measures variation in the number of clicks of the rotating plate 134, and the second A/D converter 234 converts the variation into digital data. The resulting digital data is calculated as real-time variation data by the encoder variation calculation unit 236.

In this embodiment, data about the user's backbone necessary for the functionality of the thermotherapy device is calculated by combining the variation of the encoder variation calculation unit 236 with the variation of the motor variation calculation unit 226 at a subsequent step.

4). User's Backbone Information Generation Step (S240):

This embodiment includes user's backbone information generation step S240 of obtaining the user's primary backbone information by combining the real-time motor variation data with the real-time encoder variation data, and creating the user's secondary backbone information by inference by comparing the primary backbone information with data entered in the standard backbone information database.

In this embodiment, the data operation unit 242 is supplied with the real-time encoder variation and the real-time motor variation, and performs an operation on the variations by combining them with each other. The data operation unit 242 graphs variation in load applied to the transfer motor 122 with respect to the variation of the encoder 132. The control unit 150 inputs the data graphed by the data operation unit 242 to the data search unit 244, which corresponds to a subsequent stage.

In this embodiment, the data search unit 244 searches for necessary information using the real-time data obtained by the data operation unit 242. It is preferred that the data search unit 244 search for the reflection points of voltage variation using the voltage variation of the motor as real-time motor variation. The points found at this step are stored in the third memory 248.

In this embodiment, the backbone information calculation unit 246 calculates the user's primary backbone information based on search information input by the data search unit 244.

In the user's primary backbone information, a location at which the voltage variation of the motor forms a first highest peak is calculated as the location of the user's thoracic vertebra No. 3. The location of the second highest peak of the voltage variation of the motor is calculated as the location of the user's lumbar vertebra No. 5. A downward curve is formed between the location of thoracic vertebra No. 3 and the location of lumbar vertebra No. 5, a lowest peak is formed, and then a rising curve is formed again. In this embodiment, the reason why the location of the first highest peak of the voltage variation is selected as the location of the user's thoracic vertebra No. 3 and the reason why the location of the second highest peak of the voltage variation is selected as the location of the user's lumbar vertebra No. 5 become clear through the following experimental data.

In this embodiment, when the location of the user's thoracic vertebra No. 3 and the location of the user's lumbar vertebra No. 5 are determined, the backbone information calculation unit 246 obtains the user's backbone information by inference based on the location of thoracic vertebra No. 3 and the location of lumbar vertebra No. 5. A method of inferring the user's backbone information is based on the user's primary backbone information (the location of thoracic vertebra No. 3 and the location of lumbar vertebra No. 5). However, a method of creating the user's secondary backbone information by comparing the primary backbone information with standard backbone information input in advance may be performed.

A method of scanning a user's human body using the thermotherapy device 100 will be described below as the most preferred embodiment.

FIGS. 7 to 11 are graphs showing variations in the voltage of the transfer motor 122 measured during the use of the thermotherapy device.

FIG. 12 is a schematic diagram of a model of the backbone of the human body.

Here, in the method of scanning the user's human body, a bed-type thermotherapy device 100 was used, the variation of the transfer motor 122 was based on variation in the voltage value of the transfer motor 122 that occurred during the movement of the thermo-ceramic unit 110, and also variation in the number of clicks of the encoder 132 was used as a reference.

<<Correlations Between Shapes of Users' Backbones and Variations in Voltage of Transfer Motor>>

In this embodiment, the correlations between the shapes of users' backbones and variations in the voltage of the transfer motor 122 are objectively supported by the following experiments and their experimental results.

<(1). Correlations Between Body Conditions of Experimental Participants and Variations in Voltage of Transfer Motor>

A plurality of experimental participants having different heights and weights was arbitrarily selected, and the differences between voltages applied to the transfer motor unit 120 when the experimental participants used the bed-type thermotherapy device 100 were measured.

Although the total number of persons who participated in the experiments of this embodiment was 18, a list of finally determined participants and the lengths and weights of their bodies are as shown in Table 1. The bed-type thermotherapy device used was a product (Model label: CERAGEM-3500) of a company to which the inventors of the present invention belonged. The experimental participants had different heights and weights, as shown in Table 1:

TABLE 1

| Name | *-hui Kim | *-gi Lee | *-han Kim | *-won Choi | *-seung Lee | *-su Park | *-seon Oh |
|---|---|---|---|---|---|---|---|
| Height (cm) | 168 | 160 | 173 | 182 | 180 | 178 | 153 |
| Weight (kg) | 68.2 | 63.4 | 90.1 | 68.6 | 67.5 | 84.3 | 41.8 |

| Name | *-hui Kim | *-u Yu | *-rok Kim | *-ui Choi | *-ho Choi | *-yeon Jeon | *-chan Gang |
|---|---|---|---|---|---|---|---|
| Height (cm) | 163 | 170 | 175 | 170 | 175 | 175 | 178 |
| Weight (kg) | 47.5 | 65.2 | 80.2 | 77.5 | 82.3 | 82.1 | 82.1 |

<(2). Experimental Method>

The experiments were conducted in the following way. Each of the experimental participants was asked to lie down on the bed-type thermotherapy device 100, with the head of the experimental participant being directed toward the upper end limit switch 163 installed inside the main mat 101, and with the buttocks of the experimental participant being directed toward the lower end limit switch 164 installed inside the main mat 101. In this state, the thermo-ceramic unit 110 installed inside the main mat 101 was moved from an upper limit to a lower limit using the remote controller 162, and variations in the voltage of the transfer motor 122 were measured in real time during the movement. Furthermore, the variations of the encoder 132 were measured based on the number of clicks by the encoder data measurement unit 232.

<(3). Results of Experiments>

The correlations between the variations in the voltage of the transfer motor 122 and the variations of the encoder 132 were discussed based on the variations in the voltage of the transfer motor 122 and the variations of the encoder 132. For this purpose, the correlations were discussed with the variation of the encoder 132 set to the X axis and the variation of the transfer motor 122 set to the Y axis. The correlations were objectively observed using Japanese Hioki company's measuring equipment (product name: MEMORY HiCORDER).

FIGS. 7 to 11 are graphs showing the correlations between variations in voltage applied to the transfer motor 122 and distances (elapsed times) measured via the encoder 132 for each of the experimental participants.

From the results of the experiments, it can be seen that differences in voltage were exhibited depending on the heights and/or weights of the experimental participants. However, these differences correspond to a common phenomenon, and are only quantitative differences but cannot be considered to be qualitative differences.

In contrast, one fact which was common to all experimental data was found. It is the fact that voltage gradually rose and then formed a first peak in an early state in which the thermo-ceramic unit 110 moved, gradually dropped and continued, and rose again and then formed a final peak in the final stage. This phenomenon was common to experimental participants whose heights are in the range from 153 cm to 182 cm and also to experimental participants whose weights are in the range from 41.5 Kg to 90.1 Kg. This was considered to mean that the present invention could be applied to almost all users when the fact that general users had the above-described body conditions was taken into consideration.

<(4). Results of Experiments: Correlations Between Common Peaks>

Meanwhile, from the drawings of FIGS. 7 to 11 obtained as a result of the experiments, it can be seen that regardless of the body conditions of users and in common, the thermo-ceramic unit 110 moved somewhat, formed a first peak, proceeded, and then formed a second peak. Since this phenomenon resulted from the correlations between the thermo-ceramic unit 110 and the users' backbones, the correlations will be discussed below.

In this embodiment, according to the experimental method, points at which the thermo-ceramic unit 110 comes into contact with the backbone of each experimental participant are two points that are laterally spaced apart from the center of the backbone of the experimental participant by about 5 cm to 15 cm, and peanut-shaped heating units move along a succession of two points while rotating. During the movement, the thermo-ceramic unit 110 moves along the curve of the user's backbone, and the transfer motor 122 varies the voltage value thereof. In this case, load is gradually applied to the transfer motor 122 when the thermo-ceramic unit 110 starts to move along the neck of the experimental participant, the highest load is applied when the thermo-ceramic unit 110 comes into contact with the experimental participant's shoulder blade, the load decreases after the thermo-ceramic unit 110 passes the shoulder blade, and higher load is applied again when the thermo-ceramic unit 110 comes into contact with the ilium of the experimental participant. This phenomenon accurately conforms to the skeleton structure of the backbone of the human body.

FIG. 12 is a diagram schematically illustrating the backbone of the human body. As can be understood from FIG. 12, the backbone of the human body may be divided into the cervical vertebra portion, the thoracic vertebra portion and the lumbar vertebra portion, and the locations at which they are placed correspond to the shoulder blade and ilium of the human body. In light of the skeleton structure of the human body, the first peak corresponds to thoracic vertebra No. 3, and the final peak corresponds to lumbar vertebra No. 5.

Accordingly, in this embodiment, it is preferable to contrast the voltages measured in real time at data measurement step S210 with each other, and then estimate the location of the first highest peak of the voltage to the location of the user's thoracic vertebra No. 3 and the location of the second highest peak of the voltage to be the location of the user's lumbar vertebra No. 5.

<<Correlations Regarding Usability of Standard Backbone Information>>

<(1). Measurement of User's Backbone Data>

The experimenters arbitrarily selected a plurality of experimental participants having different heights, and performed X-ray imaging on the experimental participants in order to measure the shapes of their backbones. The experimental participants were 14 persons presented in Table 1, who were arbitrarily selected males and females having heights in the range from 153 cm to 182 cm and weights in the range from 41.5 Kg to 90.1 Kg. The X-ray imaging was performed in 00 radiologic clinic which was located Sanbu-dong, Cheonan-si, Chungcheongnam-do, Korea. The measurement was performed using a method of manually measuring printed X-ray photos and recording data.

The backbone data that was acquired from the 14 experimental participants by the experimenters based on their X-ray photos is shown in the following Table 2:

TABLE 2

| | *_hui Kim mm | *_gi Lee mm | *_han Kim mm | *_won Choi mm | *_seung Lee mm | *_su Park mm | *_seon Oh mm | *_hui Kim mm | *_u Yu mm | *_rok Kim mm | *_ui Choi mm | *_ho Choi mm | *_yeon Jeon mm | *_chan Gang mm |
|---|---|---|---|---|---|---|---|---|---|---|---|---|---|---|
| CV 1 | 20.00 | 18.00 | 20.00 | 23.00 | 24.00 | 21.00 | 18.00 | 21.00 | 18.00 | 23.00 | 19.00 | 19.00 | 25.00 | 20.00 |
| CV 2 | 24.00 | 24.00 | 24.00 | 24.00 | 23.00 | 24.00 | 23.00 | 24.00 | 24.00 | 24.00 | 24.00 | 25.00 | 26.00 | 24.00 |
| CV 3 | 17.00 | 18.00 | 20.00 | 20.00 | 20.00 | 18.00 | 14.00 | 16.00 | 18.00 | 18.00 | 19.00 | 20.00 | 20.00 | 18.00 |
| CV 4 | 18.00 | 18.00 | 19.00 | 20.00 | 20.00 | 20.00 | 14.00 | 16.00 | 18.00 | 18.00 | 20.00 | 17.00 | 19.00 | 18.00 |
| CV 5 | 15.00 | 17.00 | 18.00 | 20.00 | 20.00 | 19.00 | 16.00 | 18.00 | 17.00 | 19.00 | 17.00 | 19.00 | 17.00 | 22.00 |
| CV 6 | 18.00 | 17.00 | 21.00 | 21.00 | 20.00 | 21.00 | 15.00 | 17.00 | 19.00 | 19.00 | 18.00 | 19.00 | 19.00 | 20.00 |
| CV 7 | 18.00 | 18.00 | 20.00 | 20.00 | 21.00 | 23.00 | 15.00 | 17.00 | 22.00 | 19.00 | 19.00 | 21.00 | 22.00 | 20.00 |
| TV 1 | 20.00 | 20.00 | 21.00 | 22.00 | 22.00 | 23.00 | 16.00 | 23.00 | 21.00 | 21.00 | 21.00 | 23.00 | 22.00 | 23.00 |
| TV 2 | 21.00 | 21.00 | 21.00 | 23.00 | 25.00 | 22.00 | 19.00 | 18.00 | 22.00 | 22.00 | 23.00 | 24.00 | 22.00 | 22.00 |
| TV 3 | 22.00 | 22.00 | 23.00 | 25.00 | 24.00 | 22.00 | 18.00 | 23.00 | 22.00 | 22.00 | 21.00 | 22.00 | 24.00 | 25.00 |
| TV 4 | 21.00 | 22.00 | 23.00 | 25.00 | 27.00 | 24.00 | 20.00 | 22.00 | 22.00 | 24.00 | 23.00 | 23.00 | 24.00 | 25.00 |
| TV 5 | 22.00 | 23.00 | 23.00 | 23.00 | 26.00 | 22.00 | 20.00 | 22.00 | 23.00 | 24.00 | 23.00 | 24.00 | 23.00 | 25.00 |
| TV 6 | 21.00 | 24.00 | 23.00 | 23.00 | 26.00 | 23.00 | 20.00 | 22.00 | 23.00 | 24.00 | 24.00 | 25.00 | 25.00 | 22.00 |
| TV 7 | 23.00 | 23.00 | 25.00 | 26.00 | 26.00 | 26.00 | 21.00 | 22.00 | 24.00 | 23.00 | 25.00 | 26.00 | 27.00 | 23.00 |
| TV 8 | 25.00 | 24.00 | 24.00 | 24.00 | 27.00 | 26.00 | 21.00 | 22.00 | 24.00 | 27.00 | 25.00 | 27.00 | 25.00 | 27.00 |
| TV 9 | 25.00 | 25.00 | 23.00 | 28.00 | 28.00 | 28.00 | 22.00 | 24.00 | 25.00 | 25.00 | 26.00 | 27.00 | 27.00 | 26.00 |
| TV 10 | 26.00 | 25.00 | 29.00 | 28.00 | 29.00 | 31.00 | 23.00 | 27.00 | 28.00 | 30.00 | 26.00 | 30.00 | 30.00 | 30.00 |
| TV 11 | 27.00 | 28.00 | 31.00 | 30.00 | 31.00 | 34.00 | 25.00 | 29.00 | 30.00 | 29.00 | 29.00 | 30.00 | 30.00 | 31.00 |
| TV 12 | 30.00 | 29.00 | 30.00 | 33.00 | 30.00 | 36.00 | 27.00 | 32.00 | 30.00 | 33.00 | 30.00 | 32.00 | 33.00 | 31.00 |
| LV 1 | 33.00 | 29.00 | 33.00 | 35.00 | 36.00 | 39.00 | 30.00 | 33.00 | 34.00 | 35.00 | 34.00 | 33.00 | 39.00 | 38.00 |
| LV 2 | 37.00 | 35.00 | 38.00 | 38.00 | 35.00 | 42.00 | 33.00 | 36.00 | 34.00 | 38.00 | 35.00 | 36.00 | 37.00 | 36.00 |
| LV 3 | 37.00 | 38.00 | 36.00 | 40.00 | 40.00 | 42.00 | 33.00 | 36.00 | 37.00 | 41.00 | 38.00 | 38.00 | 38.00 | 37.00 |

TABLE 2-continued

| | *_hui Kim mm | *_gi Lee mm | *_han Kim mm | *_won Choi mm | *_seung Lee mm | *_su Park mm | *_seon Oh mm | *_hui Kim mm | *_u Yu mm | *_rok Kim mm | *_ui Choi mm | *_ho Choi mm | *_yeon Jeon mm | *_chan Gang mm |
|---|---|---|---|---|---|---|---|---|---|---|---|---|---|---|
| LV 4 | 37.00 | 37.00 | 39.00 | 41.00 | 40.00 | 42.00 | 35.00 | 37.00 | 39.00 | 42.00 | 38.00 | 38.00 | 38.00 | 39.00 |
| LV 5 | 37.00 | 39.00 | 39.00 | 43.00 | 40.00 | 42.00 | 35.00 | 36.00 | 39.00 | 41.00 | 38.00 | 43.00 | 42.00 | 44.00 |
| Entire Backbone | 590 | 594 | 623 | 655 | 660 | 661 | 533 | 597 | 604 | 641 | 615 | 646 | 658 | 645 |

In Table 1, "CV 1" is cervical vertebra No. 1, "CV 2" is cervical vertebra No. 2, "TV 1" is thoracic vertebra No. 1, "TV 2" is a thoracic vertebra No. 2, "LV 1" is lumbar vertebra No. 1, and "LV 2" is lumbar vertebra No. 2.

<(2). Modeling of Average Shape of User's Backbones>

The experimenters calculated the average length of each of vertebrae spanning from cervical vertebra No. 1 to lumbar vertebra No. 5 based on the data of Table 2. The calculated average length may be considered to be the users' average backbone length. Furthermore, the relative lengths of respective vertebrae were calculated. Here, on condition that the length of thoracic vertebra No. 3 was set to 1.00, the relative lengths of the respective vertebra were calculated. When the relative lengths of the respective vertebrae are calculated, the data may be usefully used to determine the length of a target backbone and/or the length of a target vertebra, and the location of the backbone and/or the location of the vertebra. Based on Table 2, the average length of vertebrae and the relative lengths of the respective vertebrae are shown in the following Table 3:

TABLE 3

| Class | Cervical vertebrae | | | | | | | Thoracic vertebrae | | | | |
|---|---|---|---|---|---|---|---|---|---|---|---|---|
| No. | 1 | 2 | 3 | 4 | 5 | 6 | 7 | 1 | 2 | 3 | 4 | 5 |
| Average length (mm) | 20.5 | 24.1 | 18.3 | 18.2 | 18.0 | 18.8 | 19.7 | 21.3 | 21.8 | 22.5 | 23.1 | 23.0 |
| Relative length (%) | 91.1 | 107 | 81.3 | 80.9 | 80.0 | 83.6 | 87.6 | 94.7 | 96.9 | 100 | 103 | 102 |

| Class | Thoracic vertebrae | | | | | | | Lumbar vertebrae | | | | |
|---|---|---|---|---|---|---|---|---|---|---|---|---|
| No. | 6 | 7 | 8 | 9 | 10 | 11 | 12 | 1 | 2 | 3 | 4 | 5 |
| Average length (mm) | 23.1 | 24.4 | 25.1 | 25.7 | 27.8 | 29.6 | 30.8 | 34.1 | 35.8 | 37.7 | 39.1 | 39.8 |
| Relative length (%) | 102 | 108 | 112 | 114 | 123 | 132 | 137 | 151 | 159 | 168 | 174 | 177 |

<(3). Usability of Standard Backbone Information>

Table 3 lists the relative lengths of the vertebrae of the backbone that were calculated based on the actually measured data of Table 2. Table 3 is based on a case in which a population is experimental participants, and does not consider the distinction of gender, area or age. If more participants form a population, more accurate estimated values can be calculated. In this regard, the standard backbone information may be constructed based on a small population as in the experiments of this embodiment, information that was previously constructed and used by a government or a public organization may be utilized in order to acquire more accurate data. The standard backbone information may be divided according to area, country, continent, age or gender.

Since this embodiment enables the average backbone length of users to be estimated and the length of each vertebra to be calculated based on the standard backbone information, it may be applied to the thermotherapy device in practice and be then used.

For example, when the user lies down on the main mat 101 and makes a scan by moving the thermo-ceramic unit 110 along his or her back, the user can automatically become aware of the locations of his or her thoracic vertebra No. 3 and lumbar vertebra No. 5, and can automatically become aware of the entire length of the user's backbone, the length of each vertebra, and the location of each vertebra based on the locations.

In this state, this embodiment enables the user to select and use a curved rail suitable for the shape of his or her backbone, to set the conditions of use so that the thermo-ceramic unit 110 can be raised or lowered at a specific location according to a program installed in the control unit, and to input and use the suitable conditions of the use of the thermotherapy device.

While the thermotherapy device and the method of operating the same according to the embodiments have been specifically described, the description illustrates only the most preferred embodiments of the present invention, but the present invention is not limited thereto. The scope of the present invention is determined and limited by the attached claims.

Furthermore, those having ordinary knowledge in the art could make a variety of modifications and variations based on the description of the specification, and it is apparent that the modifications and the variations do not depart from the scope of the present invention.

What is claimed is:

1. A thermotherapy device having a human body scan function, comprising:
   a thermo-ceramic unit (110);
   a transfer motor unit (120) configured to make the thermo-ceramic unit (110) move along a longitudinal direction of a user's backbone;
   a motor variation generation module (220) configured to measure variations in load of the transfer motor unit (120); and
   a backbone information generation module (240) configured to generate information about a shape of the user's backbone using the measured variations of the motor variation generation module (220).

2. The thermotherapy device of claim 1, further comprising:
   an encoder unit (130) configured to count an rpm of the transfer motor (122); and
   an encoder variation generation module (230) configured to measure a distance that the thermo-ceramic unit (110) moves using data of the encoder unit (130).

3. The thermotherapy device of claim 2, wherein the backbone information generation module (240) receives data from the motor variation generation module (220) and the encoder variation generation module (230), and generates the user's backbone-related information including a length of the user's backbone and a length of each vertebra of the user's backbone.

4. The thermotherapy device of claim 1, wherein the measurement of the variations in load of the transfer motor unit (120) is performed using variations in at least any one of voltage, current and power of the transfer motor (122).

5. The thermotherapy device of claim 1, wherein:
   the motor variation generation module (220) is a motor data measurement unit (222) configured to measure variations in load of the transfer motor unit (120) via variations in current of the transfer motor (122); and
   the motor variation generation module (220) comprises a resistance unit (124) configured to convert the variations in current of the transfer motor (122) into variations in voltage variation, and a first analog-to-digital (A/D) conversion unit (224) configured to convert the variations in voltage into digitized data.

6. The thermotherapy device of claim 1, wherein:
   the backbone information generation module (240) is a backbone information calculation unit (246) configured to generate information about the user's backbone; and
   the backbone information calculation unit (246) generates the information about the user's backbone using primary information about the user's backbone that is acquired while the thermo-ceramic unit (110) is moving and data entered in a standard backbone information database.

7. The thermotherapy device of claim 6, wherein the primary information is lengths from the user's head to two or more points that are spaced apart on the user's backbone.

8. The thermotherapy device of claim 7, wherein if the points are two in number, a first point thereof corresponds to thoracic vertebra No. 3 and a second point thereof corresponds to lumbar vertebra No. 5.

9. The thermotherapy device of claim 6, wherein the data entered in the standard backbone information database is a length of each vertebra with respect to a length of thoracic vertebra No. 3.

10. The thermotherapy device of claim 6, wherein the backbone information generation module (240) comprises a data operation unit (242) configured to receive data from the motor variation calculation unit (220) and the encoder variation calculation unit (230), and a data search unit (244) configured to search for information in the data received from the data operation unit (242), and to transfer the found information to the backbone information calculation unit (246).

11. The thermotherapy device of claim 10, wherein the data operation unit (242) graphs variations in load applied to the transfer motor (122) with respect to variations of the encoder (132), and transfers the graph to the data search unit (242).

12. The thermotherapy device of claim 11, wherein the data search unit (244) transfers information found via one or more reflection points of the graph to the backbone information calculation unit (246).

13. A human body scan method for a thermotherapy device, comprising:
   preparation step (S210) of inputting user information and making preparation;
   data measurement step (S220) of measuring variations in load of a transfer motor (122) and variations of an encoder (132) which counts an rpm of the transfer motor (122) while reciprocating a thermo-ceramic unit (110);
   data conversion step (S230) of receiving the measured variations in load and the variations of the encoder and converting the measured variations in load and the variations of the encoder into data; and
   backbone information generation step (S240) of receiving the resulting data and generating a shape of the user's backbone using the resulting data.

14. The human body scan method of claim 13, wherein the backbone information generation step (S240) comprises acquiring primary information about the user's backbone from the received data, and generating information about the user's backbone using the acquired primary information and data entered in a standard backbone information database.

15. The human body scan method of claim 14, wherein the primary information is lengths from the user's head to two or more points that are spaced apart on the user's backbone.

16. The human body scan method of claim 15, wherein if the points are two in number, a first point thereof corresponds to thoracic vertebra No. 3 and a second point thereof corresponds to lumbar vertebra No. 5.

17. The human body scan method of claim 16, wherein the data entered in the standard backbone information database is a length of each vertebra with respect to a length of thoracic vertebra No. 3.

* * * * *